(12) United States Patent
Zhang et al.

(10) Patent No.: US 8,877,777 B2
(45) Date of Patent: Nov. 4, 2014

(54) PROCESS FOR PURIFYING CYCLOLIPOPEPTIDE COMPOUNDS OR THE SALTS THEREOF

(75) Inventors: Zhaoli Zhang, Shanghai (CN); Shidong Liu, Shanghai (CN); Zhonghao Zhuo, Shanghai (CN); Xiaoming Ji, Shanghai (CN)

(73) Assignee: Shanghai Techwell Biopharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 13/877,141

(22) PCT Filed: Sep. 27, 2011

(86) PCT No.: PCT/CN2011/080227
§ 371 (c)(1),
(2), (4) Date: Jun. 25, 2013

(87) PCT Pub. No.: WO2012/041220
PCT Pub. Date: Apr. 5, 2012

(65) Prior Publication Data
US 2013/0296529 A1 Nov. 7, 2013

(30) Foreign Application Priority Data
Sep. 30, 2010 (CN) .......................... 2010 1 0298554

(51) Int. Cl.
| | | |
|---|---|---|
| A61K 38/12 | (2006.01) | |
| C07K 5/00 | (2006.01) | |
| C07K 7/00 | (2006.01) | |
| C07K 16/00 | (2006.01) | |
| C07K 17/00 | (2006.01) | |
| C07K 7/56 | (2006.01) | |

(52) U.S. Cl.
CPC ........................................ C07K 7/56 (2013.01)
USPC ........................................................ 514/317

(58) Field of Classification Search
None
See application file for complete search history.

(56) References Cited

FOREIGN PATENT DOCUMENTS

| | | |
|---|---|---|
| EP | 0431350 A1 * | 6/1991 |
| EP | 0486011 A2 | 5/1992 |
| GB | 1320156 A | 6/1973 |
| WO | WO 2012/041220 | 5/2012 |

OTHER PUBLICATIONS

Kanasaki et al "FR209602 and Related Compounds, Novel Antifungal Lipopeptides from Coleophoma craterformis No. 738" J Antibiotics 59:137-144. Published 2006.*

Fujie A "Discovery of micafungin (FK463): A novel antifungal drug derived from a natural product lead" Pure Appl. Chem. 79:603-614. Published 2007.*

PCT International Search Report and Written Opinion dated Dec. 29, 2011 issued in PCT/CN2011/080227 (WO/2012/041218).

Iwamoto et al. (1994) "WF 11899 A, B and C, Novel Antifungal Lipopeptides I. Taxonomy, Fermentation, Isolation and Physicochemical Properties" *The Journal of Antibiotics*. 10(47): 1084-1091.

* cited by examiner

*Primary Examiner* — Maury Audet
*Assistant Examiner* — Zachary J Miknis
(74) *Attorney, Agent, or Firm* — Tom Hunter; Weaver Austin Villeneuve & Sampson LLP

(57) ABSTRACT

A method for purifying a cyclic lipopeptide or a salt thereof is provided. The method comprises the steps: (1) extracting a fermentation broth containing a compound of formula I or a salt thereof, to obtain an extract 1 after filtration or centrifugation; (2) diluting or concentrating the extract 1 under vacuum to decrease the content of the organic solvent, to obtain an extract 2; (3) loading the extract 2 onto a macroporous absorption resin; (4) washing the macroporous adsorption resin with water, an organic solvent, or a mixture of water and an organic solvent as a washing solution; and (5) eluting the compound of formula I off from the macroporous adsorption resin with water, an organic solvent, or a mixture of water and an organic solvent as a washing solution as an eluant. Compared with the prior art, the purification method has the advantages that fewer organic solvent is used, no silica gel is used, the harm to the environment is less, and the purity of the collected compound of formula I is improved.

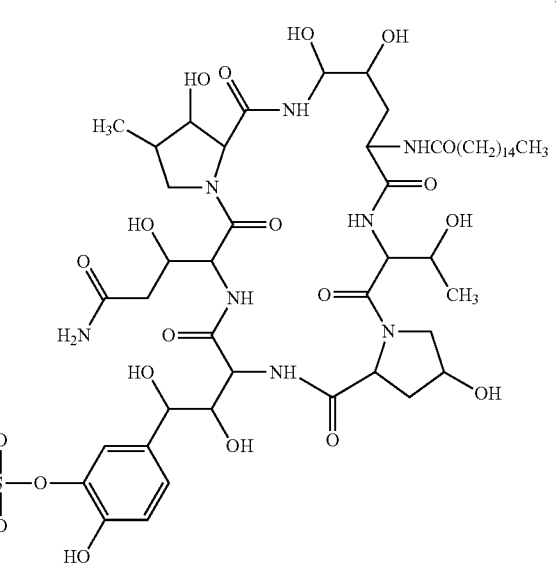

13 Claims, 1 Drawing Sheet

PROCESS FOR PURIFYING CYCLOLIPOPEPTIDE COMPOUNDS OR THE SALTS THEREOF

CROSS-REFERENCE TO RELATED APPLICATIONS

This application is a 371 National Phase of PCT/CN2011/080227, filed on Sep. 27, 2011, which claims benefit of and priority to CN 201010298554.6, filed on Sep. 30, 2010, which is incorporated herein by reference in its entirety for all purposes.

TECHNICAL FIELD

The present invention relates to the field of organic chemistry, particularly, to the process for purifying the cyclolipopeptide compound of Formula I or the salts thereof.

BACKGROUND

Fungal-infections have become the major cause for the high incidence and mortality in immunodeficiency patients. During the past 20 years, the incidence of mycotic infection has increased significantly. The high-risk population for the fungal-infection includes critical patients, surgical patients and the patients with HIV-infection, leukemia as well as other tumors. Additionally, the organ transplant recipients are also the high-risk population for fungal-infection.

The echinocandins are novel anti-fungal medicaments, which are effective in treating *Candida*- or *aspergillus*-infections, and the examples of which are Caspofungin and Micafungin. The echinocandins inhibit the fungi by inhibiting the formation of 1,3-β glucosidic bond, thereby reducing the toxicity toward the human and the side effects, while maintaining high efficiency. Therefore, compared with the traditional antifungal-medicaments, the echinocandins are safer when they are used.

FK463 (Micafungin) is the compound of Formula III, which is obtained by removing the side-chain of the precursor, compound FR901379 of Formula I ($M_0$) through an enzyme reaction, thus forming compound FR179642 ($M_1$) of Formula II by chemical modification. Therefore, the compound of Formula I with high-purity is very important for obtaining Micafungin with high-purity.

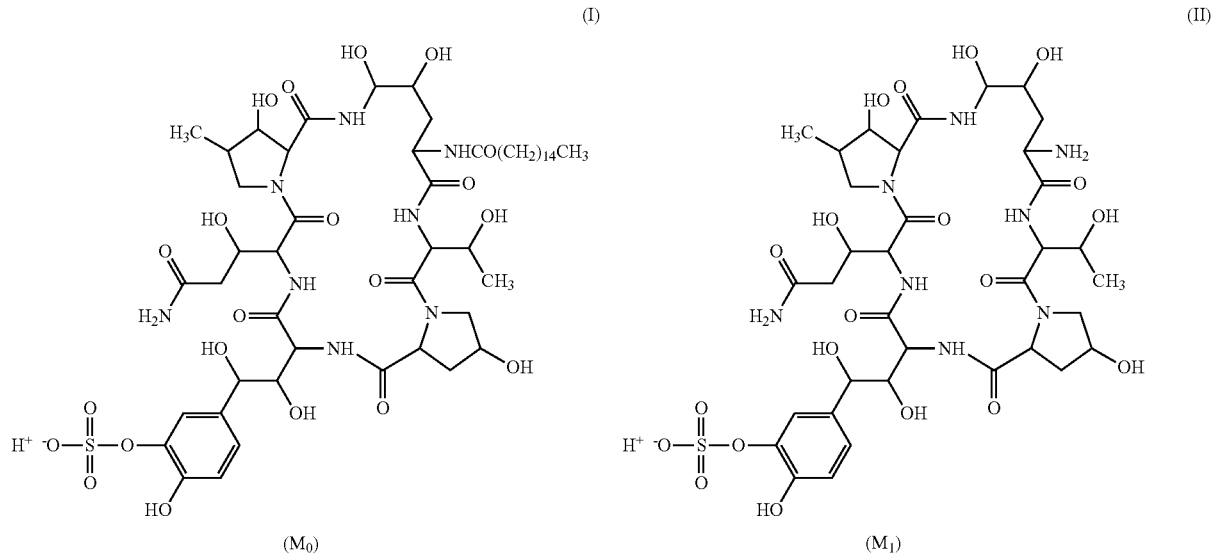

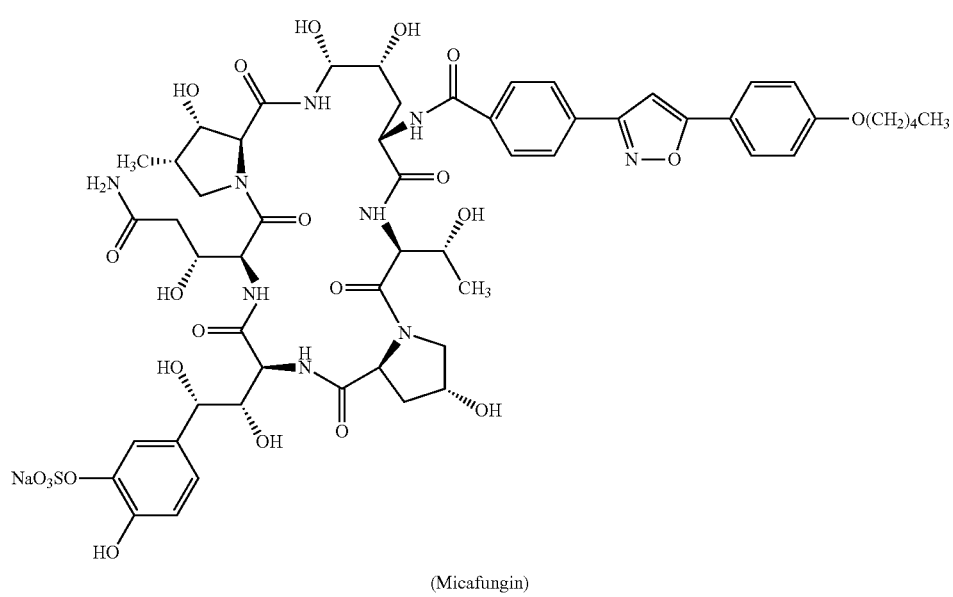

(Micafungin)

EP0431350B1 has disclosed a method for purifying the compound of Formula I, wherein, the method comprises the following steps: the fermentation liquid is extracted by acetone; the filtrate is concentrated for removing acetone, washed by ethyl acetate, and extracted by n-butanol; the n-butanol phase is concentrated to dryness; and the compound of Formula I is obtained by silica gel chromatography. For this method, great amount of organic solvent is needed, and silica gel which will not be degraded and severely pollute the environment is used, therefore, such method will be adverse to the environment protection, be harmful to the physical healthy of the operators, and not suitable for large-scale production.

Therefore, it is urgent in the art to find a purification method without using great amount of solvent and silica gel, and such method can not only overcome the defects in the prior art, but improve the purity of the compound of Formula I.

SUMMARY OF THE INVENTION

The subject of the present invention is to provide a process for purifying the compound of Formula I.

In the present invention, a process for purifying the compound of Formula I or the salts thereof is provided, said process comprising the following steps:

(1) mixing the fermentation liquid comprising the compound of Formula I or the salts thereof with an organic solvent for extracting the fermentation liquid, and obtaining extract 1 by filtration or centrifugation;

(2) diluting or concentrating extract 1 in vacuum for reducing the content of the organic solvent, thereby obtaining extract 2;

(3) loading extract 2 onto a macroporous adsorption resin;

(4) washing the macroporous adsorption resin by using water, an organic solvent or a mixed solution of an organic solvent and water as the washing liquid; and (5) eluting the compound of Formula I from the macroporous adsorption resin using water, an organic solvent or a mixed solution of an organic solvent and water as eluent.

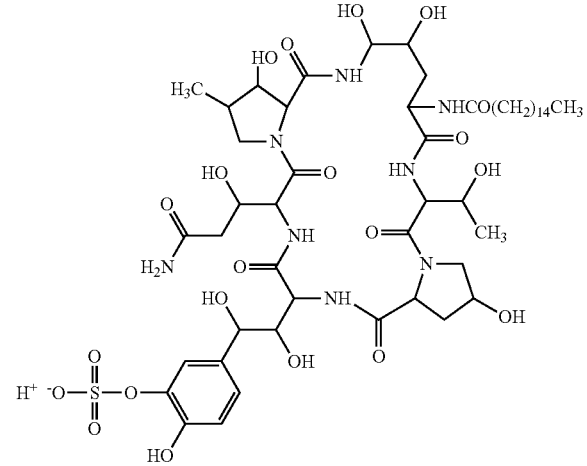

In the purification process provided by the invention, in step (3), extract 2 is allowed to flow through the chromatographic column filled with the macroporous adsorption resin, or the macroporous adsorption resin is directly fed into the extract comprising the compound of Formula I, and the resulting mixture is agitated for 5-120 mins, thereby loading extract 2 comprising the compound of Formula I onto the macroporous adsorption resin; and the flow rate is 0.1-10 column volumes per hour.

In the purification process provided by the invention, the fermentation liquid in step (1) includes the mycelia obtained from the fermentation liquid upon filtration or centrifugation.

In the purification process provided by the invention, in step (2), the volume percentage of the organic solvent is 0-40%, based on the total volume of extract 2.

In the purification process provided by the invention, in step (3), the weight ratio of the crude compound of Formula I to the macroporous adsorption resin is 0.1-1.0:100 (g/ml).

In the purification process provided by the invention, in step (4), the volume percentage of the organic solvent is 0-40%, preferably 20-40%, based on the total volume of the washing liquid.

In the purification process provided by the invention, in step (5), the volume percentage of the organic solvent is 40-90%, preferably 40-60%, based on the total volume of the eluent.

In the purification process provided by the invention, the macroporous adsorption resin is selected from a non-polar aromatic adsorption resin polymerized from styrene and divinylbenzene, or a methacrylic adsorption resin of moderate polarity with methacrylate units in its structure.

In another preferred embodiment, the adsorption resin is selected from: XAD-1, XAD-2, XAD-3, XAD-4, XAD-5, XAD-16, XAD-16HP, HP-10, HP-20, HP-20ss, HP-21, HP-30, HP-40, HP-50, SP-825, SP-850, SP-70, SP-700, SP-207, SP207ss, XAD-6, XAD-7, XAD-7HP, XAD-8, HP-2MG, or the mixture thereof.

In the purification process provided by the invention, the organic solvent is selected from: methanol, ethanol, propanol, butanol, acetone, butanone, or the mixture thereof.

Accordingly, a purification method without using great amount of solvent and silica gel is provided in the invention, and such method can not only overcome the defects in the prior art, but improve the purity of the compound of Formula I.

DETAILED DESCRIPTION OF THE INVENTION

Figure 1:
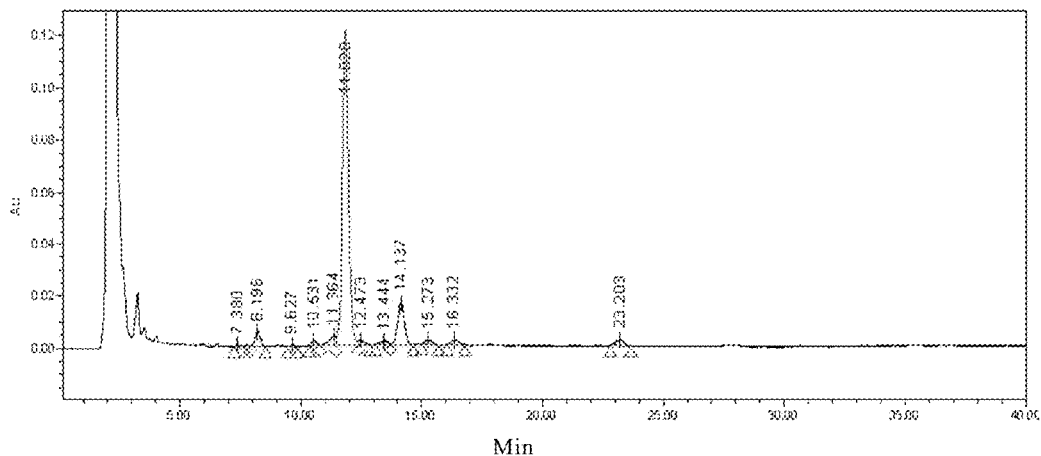
FIG. 1 shows the HPLC chromatogram of the extract comprising the compound of Formula I according to Example 1.

Through a great deal of experiments, the inventors have discovered a simple method for purifying the compound of Formula I, thereby accomplishing the present invention.

The process for purifying the compound of Formula I provided by the present invention includes the following steps:

(1) adding an organic solvent into the fermentation liquid comprising the compound of Formula I or the salts thereof for extracting the fermentation liquid, and obtaining extract 1 by filtration or centrifugation;

(2) diluting or concentrating extract 1 in vacuum for reducing the content of the organic solvent, thereby obtaining extract 2;

(3) loading extract 2 onto a macroporous adsorption resin;

(4) washing the macroporous adsorption resin by using water, an organic solvent or a mixed solution of an organic solvent and water as the washing liquid; and (5) eluting the compound of Formula I from the macroporous adsorption resin using water, an organic solvent or a mixed solution of an organic solvent and water as eluent.

Step (3) can be performed by bringing the extract comprising the compound of Formula I into contact with the macroporous adsorption resin. The contact can be performed by: a. directly feeding the adsorption resin into the extract comprising the compound of Formula I, and agitating the resulting mixture for 5-120 mins; or b. filling the chromatographic device, such as chromatographic column with the adsorption resin, and the extract comprising the compound of Formula I being allowed to flow through the chromatographic column, wherein the flow rate can be 0.1-10 column volumes per hour.

In one example of the invention, the purification process includes the following steps:

A. adding an organic solvent into the fermentation liquid comprising the compound of Formula I or the salts thereof for extracting the fermentation liquid, and obtaining extract 1 by centrifugation or filtration;

B. diluting or concentrating extract 1 in vacuum for reducing the content of the organic solvent, thereby obtaining extract 2;

C. directly feeding an adsorption resin into extract 2 comprising the compound of Formula I, and agitating the resulting mixture for 5-120 mins;

D. separating extract 2 comprising the compound of Formula I from the resin;

E. washing the macroporous adsorption resin obtained in step D using water, an organic solvent or a mixed solution of an organic solvent and water as the washing liquid; and F. eluting the washed adsorption resin obtained in step E using water, an organic solvent or a mixed solution of an organic solvent and water as the eluent, and collecting the eluate comprising the compound of Formula I, thereby obtaining the purified compound of Formula I.

In step D, the separation includes, for example filtration and centrifugation, for separating the resin from filtrate phase.

In the purification process provided by the present invention, the fermentation liquid comprising the compound of Formula I or the salts thereof in step (1) can be obtained by the methods known in the art, for example (but not limited to) fermenting *Coleophoma empetri*. F-11899 (FERM BP2635) as described in Example 1 of EP0431350B1.

In the purification process provided by the present invention, "extracting" in step (1) means directly adding an organic solvent for extracting the fermentation liquid, or filtrating the fermentation liquid for obtaining the mycelia, and adding an organic solvent for extracting the mycelia. The organic solvent is selected from: methanol, ethanol, propanol, butanol, acetone, butanone, or the mixture thereof; preferably, the organic solvent is selected from methanol, ethanol, acetone, or the mixture thereof.

In the purification process provided by the present invention, in step (2), the content of the organic solvent in extract 1 obtained in step (1) is reduced by adding water into extract 1 or concentrating extract 1 in vacuum, so that the content of the organic solvent in extract 2 is ≤40%, preferably 20%-40% (based on the total volume of extract 2).

In the purification process provided by the present invention, the organic solvent used in steps (4) and (5) is selected from: $C_{1-4}$ alcohol, $C_{1-4}$ ketone, or the mixture thereof; preferably, methanol, ethanol, propanol, butanol, acetone, butanone, or the mixture thereof.

In all of the purification processes provided by the invention, the adsorption resin is selected from a non-polar aromatic adsorption resin polymerized from styrene and divinylbenzene, or a methacrylic adsorption resin of moderate polarity with methacrylate units in its structure. Preferably, the resin is selected from: XAD series absorption resin (RohmHaas, US), Diaion HP series absorption resin (Mitsubishi Chemical Corporation, JP). More preferably, the resin is selected from: XAD-1, XAD-2, XAD-3, XAD-4, XAD-5, XAD-6, XAD-7, XAD-7HP, XAD-8, XAD-16, XAD-16HP, HP-10, HP-20, HP-20ss, HP-21, HP-30, HP-40, HP-50, HP-2MG, SP-825, SP-850, SP-70, SP-700, SP207, SP207ss, or the mixture thereof. Most preferably, the resin is selected from: HP20, XAD-16, XAD-16HP, or SP207.

In the purification process provided by the present invention, in step (4), the content of the organic solvent in the washing liquid is ≤40%, preferably 20%-40%.

In the purification process provided by the present invention, in step (5), the content of the organic solvent in the eluent is 40-90%, preferably 40%-60%.

As used herein, "compound of Formula I" or "compound I" can be used interchangeably, both referring to the compound having the following structure or the pharmaceutically acceptable salts thereof:

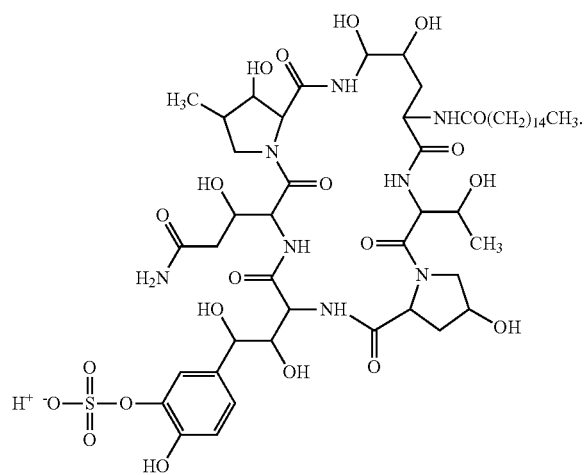

As used herein, "pharmaceutically acceptable salt" means salts formed from the following bases: inorganic base, such as sodium, potassium, magnesium, calcium, aluminium, etc.; organic base, such as methylamine, ethylamine, ethanolamine, diethanolamine, triethanolamine, cyclohexanolamine, lysine, ornithine, etc., or other bases relevant to the pharmaceutically acceptable salts.

As used herein, "purity of the compound of Formula I", "purity of compound I" and "HPLC purity of compound I" can be used interchangeably, all referring to the percentage of the peak area of compound I over the sum of all peak areas as measured under the detecting conditions of high performance liquid chromatography (HPLC) provided by the invention.

As used herein, "loading" refers to the process of bringing the extract containing the crude compound I into contact with a macroporous adsorption resin so that the compound I is adsorbed onto the macroporous adsorption resin. "Contact" includes directly feeding the macroporous adsorption resin into the solution and then agitating to allow the adsorption to occur; or filling the macroporous adsorption resin into a chromatographic device and the solution being allowed to flow through the chromatographic column.

"Washing" the macroporous adsorption resin means that a suitable buffer solution is allowed to pass through or over the macroporous adsorption resin.

As used herein, a "washing buffer solution" refers to a buffer solution used to wash the macroporous adsorption resin (mainly for removing the organic phase) before the target compound I is eluted. Conveniently, the washing buffer solution and the sample-loading buffer solution may, but not necessarily, be of the same polarity.

"Eluting" molecules from the macroporous adsorption resin means that the molecules are removed from the macroporous adsorption resin by changing the polarity of the buffer solution around the macroporous adsorption resin. Due to the polarity, the buffer solution can compete with the molecules for the adsorption sites on the macroporous adsorption resin.

As used herein, an "elution buffer solution" is used to elute the target compound I from a stationary phase. The target compound I can be eluted from the macroporous adsorption resin by the elution buffer solution.

"Purifying" the compound I from a composition comprising the target compound I and one or more non-target compounds means that the purity of compound I in the composition is increased by removing (totally or partially) at least one non-target compound from the composition.

All the features mentioned above or in the examples below of the invention can be optionally combined. All features disclosed in this specification may be used in any combination. Any alternative feature serving the same, equivalent, or similar purpose may replace each feature disclosed in this specification. Therefore, unless otherwise specified, the features as disclosed are only general examples of equivalent or similar features.

The main advantages of the invention include:

1. A novel low-cost process for purifying cyclolipopeptide compound, particularly echinocandin compounds is provided;

2. The advantages of purifying steps in the process provided by the invention, such as, simple route, mild conditions, high purification yields, simple treatments, low pollution to the environment, and the like, to a great extent, reduce the requirements on process manipulation and equipments, thereby reducing the cost.

3. Stable target products can be obtained through the process provided by the invention, thereby facilitating the quality control on final products and large-scale production;

4. The target products produced by the process provided by the invention can fulfill the requirements for transforming compound I into compound II, thereby facilitating the large-scale production of compound II and the final product, compound III.

The invention will be further illustrated with reference to the following specific examples. It is to be understood that these examples are only intended to illustrate the invention, but not to limit the scope of the invention. For the experimental methods in the following examples without particular conditions, they are performed under routine conditions or as instructed by the manufacturer. Unless otherwise specified, all percentages, ratios, proportions or parts are by weight.

The unit of the weight/volume percentages in the invention is well known to the skilled in the art, for example, the weight of a solute in a 100 mL solution.

Unless otherwise defined, all scientific and technical terms used herein have the same meaning as commonly understood by the skilled in the art. Furthermore, any process or material similar or equivalent to those described herein can be used in the process of the present invention. The preferred embodiments and materials described herein are merely provided for illustration.

In the following examples, the compound I is detected by HPLC:

Analysis is performed on Waters analytic HPLC system. Reverse-phase HPLC analysis is used for determining FR901379, Pneumocandin $B_0$ and other analogues. The material and conditions used in the reverse-phase analysis are listed as follows: CALESIL ODS chromatographic column (particle size 5 μm, 4.6 mm i.d×250 mm); temperature: 35°

C.; mobile phase: 50% acetonitrile/0.5% ammonium dihydrogen phosphate; flow rate: 1 ml/min; detected under 210 nm UV.

Example 1

2200 L of fermentation liquid comprising compound I was obtained by the method described in Example 1 of EP0431350B1. Upon filtration, 650 kg of wet mycelia was obtained. Into 65 kg of the wet mycelia, 100 L of ethanol was added for extration, the resulting mixture was filtered through plate-frame pressure filtration, the filter cake was washed, and 160 L of extract 1 comprising compound I was obtained. In extract 1, the content of compound I was 0.11 g/L, and the HPLC purity of which is 74.08% (see FIG. 1 and table 1 for the HPLC pattern).

50 L of extract 1 comprising 5.5 g compound I in total was diluted by using pure water, so that the content of ethanol was reduced to 33%, and 100 L of extract 2 comprising compound I was obtained.

Figure 2:
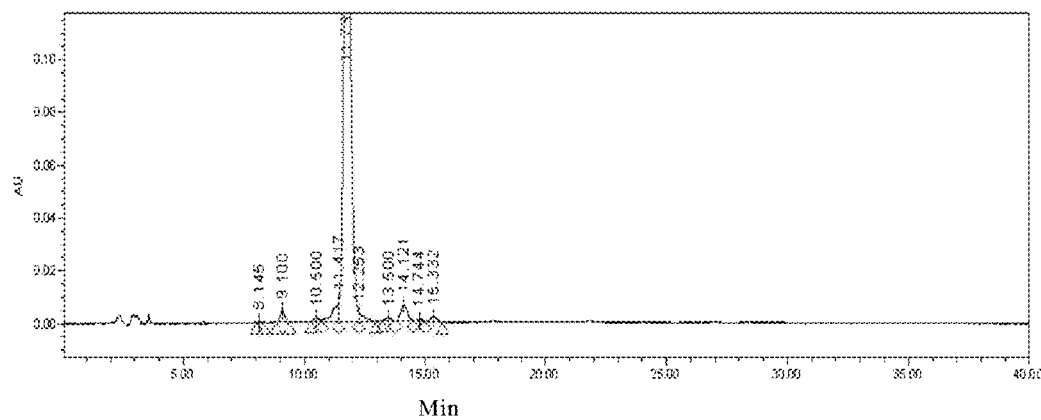
FIG. 2 shows the HPLC chromatogram of the compound of Formula I purified in Example 4.

Extract 2 comprising compound I obtained in the previous step was loaded onto a chromatographic column with 550 ml of HP20ss resin with the flow rate for loading being 3 column volumes per hour. Afterwards, 33% aqueous ethanol (2×column volumes) was used to wash the column with the flow rate for washing being 1 column volume per hour. And then, 1800 ml of 60% aqueous ethanol was used as the eluent, wherein the flow rate for eluting is 1 column volume per hour. Portions containing compound I were collected and mixed. The content of compound I in the eluate was determined as 5.2 g by HPLC (yield 94.5%), and its purity was 90.3% (see FIG. 2 and table 2 for the HPLC pattern).

TABLE 1

|   | Retention time | Area | Height | % area |
|---|---|---|---|---|
| 1 | 7.380 | 17747 | 824 | 0.63 |
| 2 | 8.196 | 86433 | 5744 | 3.07 |
| 3 | 9.627 | 11782 | 965 | 0.42 |
| 4 | 10.531 | 28138 | 2048 | 1.00 |
| 5 | 11.364 | 69799 | 3534 | 2.48 |
| 6 | 11.020 | 2087596 | 117791 | 74.08 |
| 7 | 12.473 | 32176 | 2002 | 1.14 |
| 8 | 13.444 | 34705 | 1437 | 1.23 |
| 9 | 14.137 | 316897 | 16282 | 11.25 |
| 10 | 15.273 | 33033 | 1676 | 1.17 |
| 11 | 16.332 | 40054 | 1779 | 1.42 |
| 12 | 23.203 | 59506 | 2471 | 2.11 |

TABLE 2

|   | Retention time | Area | Height | % Area |
|---|---|---|---|---|
| 1 | 8.145 | 4472 | 428 | 0.15 |
| 2 | 9.100 | 57767 | 4639 | 1.99 |
| 3 | 10.500 | 22462 | 1475 | 0.77 |
| 4 | 11.732 | 2617300 | 169214 | 90.30 |
| 5 | 13.500 | 20314 | 1138 | 0.71 |
| 6 | 14.121 | 120749 | 6234 | 3.82 |
| 7 | 14.744 | 14455 | 855 | 0.49 |
| 8 | 15.332 | 40897 | 1993 | 1.42 |

Example 2

2200 L of fermentation liquid comprising compound I was obtained by the method described in Example 1 of EP0431350B1. Into the fermentation liquid, the same volume of methanol was added for extration. Upon filtration, extract 1 comprising compound I was obtained, wherein, the content of compound I was 0.051 g/L, and the HPLC purity was 74.5%. 100 L of extract 1 comprising 5.1 g compound I in total was diluted by using pure water, so that the content of methanol was reduced to 40%, and 200 L of extract 2 comprising compound I was obtained.

Extract 2 comprising compound I obtained in the previous step was loaded onto a chromatographic column with 700 ml of XAD-16 resin with the flow rate for loading being 1 column volume per hour. Afterwards, 40% aqueous methanol (2×column volumes) was used to wash the column with the flow rate for washing being 1 column volume per hour. And then, 1800 ml of 50% aqueous methanol was used as the eluent, wherein the flow rate for eluting is 1 column volume per hour. Portions containing compound I were collected and mixed. The content of compound I in the eluate was determined as 4.7 g by HPLC (yield 92.2%), and its purity was 89.2%.

Example 3

2200 L of fermentation liquid comprising compound I was obtained by the method described in Example 1 of EP0431350B1. Into the fermentation liquid, the same volume of acetone was added for extration. Upon filtration, extract 1 comprising compound I was obtained, wherein, the content of compound I was 0.051 g/L, and the HPLC purity was 74.5%. 40 L of extract 1 comprising 2.04 g compound I in total was diluted by using pure water, so that the content of acetone was reduced to 20%, and 80 L of extract 2 comprising compound I was obtained.

Extract 2 comprising compound I obtained in the previous step was placed into a 100 L white plastic-bucket, and 1000 ml of XAD-16HP resin was added. The resulting mixture was agitated for 120 mins at the room temperature, and then filtered by a Büchner funnel on which a piece of filter paper was laid. The filtrate was discarded, and the resin was loaded on a chromatographic column. 2000 mL of 20% aqueous acetone was used to wash the column. Afterwards, the resin was eluted by 60% aqueous acetone. Portions containing compound I were collected. The content of compound I in the eluate was determined as 1.75 g by HPLC (yield 85.8%), and its purity was 90.0%.

Example 4

20 L of extract 1 comprising 2.2 g of compound I obtained in Example 1 was concentrated in vacuum, so that the content of ethanol in extract 1 was reduced to 20%, thereby obtaining 8 L of extract 2 comprising compound I.

Extract 2 comprising compound I obtained in the previous step was loaded onto a chromatographic column with 200 ml of SP207 resin with the flow rate for loading being 3 column volumes per hour. Afterwards, 20% aqueous ethanol (2×column volumes) was used to wash the column with the flow rate for washing being 1 column volume per hour. And then, 1 L of 40% aqueous ethanol was used as the eluent, wherein the flow rate for eluting is 1 column volume per hour. Portions containing compound I were collected and mixed. The content of compound I in the eluate was determined as 1.94 g by HPLC (yield 88.2%), and its purity was 89.5%.

Example 5

1450 L of extract 1 comprising 159.5 g of compound I obtained in Example 1 was diluted by using pure water, so that the content of ethanol in extract 1 was reduced to 40%, thereby obtaining 2950 L of extract 2 comprising compound I.

The crude product 2 comprising compound I obtained in the previous step was loaded onto a chromatographic column with 20 L of HP20 resin with the flow rate for loading being 10 column volumes per hour. Afterwards, 40% aqueous ethanol (2×column volumes) was used to wash the column with the flow rate for washing being 1 column volume per hour. And then, 60 L of 50% aqueous ethanol was used as the eluent, wherein the flow rate for eluting is 1 column volume per hour. Portions containing compound I were collected and mixed. The content of compound I in the eluate was determined as 145.2 g by HPLC (yield 91.0%), and its purity was 90.4%.

Example 6

50 L of extract 1 comprising 5.5 g of compound I obtained in Example 1 was diluted by using pure water, so that the content of ethanol in extract 1 was reduced to 10%, thereby obtaining extract 2 comprising compound I.

Extract 2 comprising compound I obtained in the previous step was loaded onto a chromatographic column with 550 mL of HP20 resin with the flow rate for loading being 3 column volumes per hour. Afterwards, 10% aqueous ethanol (2×column volumes) was used to wash the column with the flow rate for washing being 1 column volume per hour. And then, 1800 mL of ethanol was used as the eluent, wherein the flow rate for eluting is 1 column volume per hour. Portions containing compound I were collected and mixed. The content of compound I in the eluate was determined as 5.15 g by HPLC (yield 93.6%), and its purity was 85.4%.

Comparative Example 1

50 L of extract 1 comprising 5.5 g of compound I obtained in Example 1 was diluted by using pure water, so that the content of ethanol in extract 1 was reduced to 32%, thereby obtaining 103 L of extract 2 comprising compound I.

Extract 2 comprising compound I obtained in the previous step was loaded onto a chromatographic column with 550 mL of HP20 resin with the flow rate for loading being 10 column volumes per hour. Afterwards, 45% aqueous ethanol (2×column volumes) was used to wash the column with the flow rate for washing being 1 column volume per hour. And then, 1800 mL of 50% aqueous ethanol was used as the eluent, wherein the flow rate for eluting is 1 column volume per hour. Portions containing compound I were collected and mixed. The content of compound I in the eluate was determined as 2.13 g by HPLC (yield 38.7%), and its purity was 90.4%.

Comparative Example 2

50 L of extract 1 comprising 5.5 g of compound I obtained in Example 1 was diluted by using pure water, so that the content of ethanol in extract 1 was reduced to 45%, thereby obtaining 103 L of extract 2 comprising compound I.

Extract 2 comprising compound I obtained in the previous step was loaded onto a chromatographic column with 550 mL of HP20 resin with the flow rate for loading being 3 column volumes per hour. Afterwards, 33% aqueous ethanol (2×column volumes) was used to wash the column with the flow rate for washing being 1 column volume per hour. And then, 1800 mL of 60% aqueous ethanol was used as the eluent, wherein the flow rate for eluting is 1 column volume per hour. Portions containing compound I were collected and mixed. The content of compound I in the eluate was determined as 1.08 g by HPLC (yield 19.6%), and its purity was 85.4%.

The above examples are merely the preferred examples for the present invention, and such examples cannot be used to limit the scope of the invention. The substantial technical contents according to the present invention are broadly defined in the claims. And any entities or methods accomplished by others should be considered as the equivalents and fall within the scope as defined by the claims, if said entities or methods are the same as those defined by the claims.

The invention claimed is:
1. A method of purifying the compound of Formula I

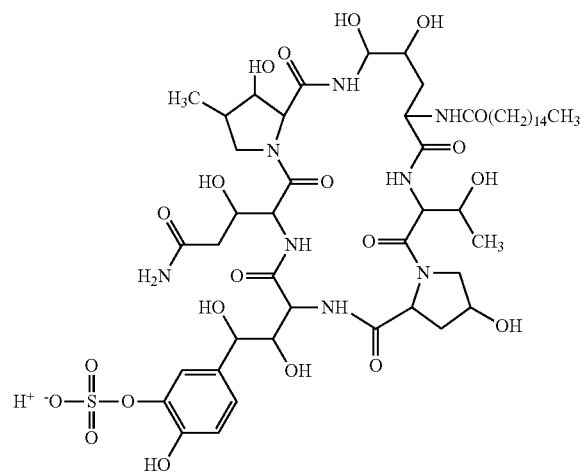

or the salts thereof, wherein said method comprises:
mixing a fermentation liquid comprising the compound of Formula I or the salts thereof with an organic solvent, and obtaining a first extract by filtration or centrifugation;
diluting said first extract or concentrating said first extract under vacuum to reduce the content of the organic solvent and thereby obtain a second extract;
loading said second extract onto a macroporous adsorption resin;
washing the macroporous adsorption resin using water, an organic solvent, or a mixed solution of an organic solvent and water as a washing liquid; and
eluting the compound of Formula I from the macroporous adsorption resin using water, an organic solvent, or a mixed solution of an organic solvent and water as eluent to provide a purified compound of Formula I or a salt thereof, wherein said organic solvent is selected from the group consisting of methanol, ethanol, propanol, butanol, acetone, and butanone.

2. The method of claim 1, wherein said loading said second extract onto a macroporous adsorption resin comprises flowing said second extract through a chromatographic column filled with the macroporous adsorption resin, or adding the macroporous adsorption resin to the second extract and agitating the resulting mixture for 5-120 minutes.

3. The method of claim 2, wherein said loading said second extract onto a macroporous adsorption resin comprises flowing said second extract through a chromatographic column filled with the macroporous adsorption resin, and the flow rate is 0.1-10 column volumes per hour.

4. The method of claim 1, wherein, said fermentation liquid includes mycelia obtained from the fermentation liquid upon filtration or centrifugation.

5. The method of claim 1, wherein the volume percentage of the organic solvent in said second extract is 0-40%, based on the total volume of said second extract.

6. The method of claim 1, wherein the weight ratio of the crude compound of Formula I to the macroporous adsorption resin when said resin is loaded is 0.1-1.0:100 (g/ml).

7. The method of claim 1, wherein the volume percentage of the organic solvent used in said washing is 0-40% based on the total volume of the washing liquid.

8. The method of claim 1, wherein in said eluting, the volume percentage of the organic solvent is 40-90% based on the total volume of the eluent.

9. The method of claim 1, wherein, the macroporous adsorption resin is selected from a non-polar aromatic adsorption resin polymerized from styrene and divinylbenzene.

10. The method of claim 9, wherein, the adsorption resin is selected from: XAD-16HP® (CAS NO: 11104-40-8), HP-20ss® (CAS NO: 9052-95-37), and, SP207ss® (CAS NO: 905310-11-4).

11. The method of claim 2, wherein said loading said second extract on a macroporous adsorption resin comprises adding the macroporous adsorption resin to the second extract and agitating the resulting mixture for 5 to 120 minutes.

12. The method of claim 1, wherein the volume percentage of the organic solvent used in said washing is 20-40%, based on the total volume of the washing liquid.

13. The method of claim 1, wherein in said eluting the volume percentage of the organic solvent 40-60% based on the total volume of the eluent.

* * * * *